United States Patent
Kauth et al.

(10) Patent No.: US 7,429,687 B2
(45) Date of Patent: Sep. 30, 2008

(54) MEDICAL DRESSING FOR OPEN CHEST WOUNDS

(75) Inventors: Mark Alan Kauth, Elgin, IL (US); Timothy Frank Camodeca, Hampshire, IL (US)

(73) Assignee: The Seaberg Company, Inc., Newport, OR (US)

( * ) Notice: Subject to any disclaimer, the term of this patent is extended or adjusted under 35 U.S.C. 154(b) by 253 days.

(21) Appl. No.: 11/503,008

(22) Filed: Aug. 10, 2006

(65) Prior Publication Data

US 2008/0033377 A1    Feb. 7, 2008

(30) Foreign Application Priority Data

Aug. 1, 2006    (GB) .................................. 0615234.2

(51) Int. Cl.
*A61F 13/00*    (2006.01)
*A61M 1/00*    (2006.01)
*A61B 17/00*    (2006.01)

(52) U.S. Cl. ...................... 602/58; 604/122; 128/887; 128/888

(58) Field of Classification Search ................. 604/122, 604/126, 304, 307, 308; 128/887, 88, 889; 137/833.21, 533.27, 543.15
See application file for complete search history.

(56) References Cited

U.S. PATENT DOCUMENTS

| | | | |
|---|---|---|---|
| 4,465,062 A | | 8/1984 | Versaggi et al. |
| 4,717,382 A | | 1/1988 | Clemens et al. |
| 5,090,406 A | | 2/1992 | Gilman |
| 5,160,322 A | | 11/1992 | Scheremet et al. |
| 5,263,922 A | * | 11/1993 | Sova et al. ................... 602/59 |
| 5,431,633 A | * | 7/1995 | Fury .......................... 604/122 |
| 5,478,333 A | | 12/1995 | Asherman, Jr. |

* cited by examiner

*Primary Examiner*—Kim M Lewis
(74) *Attorney, Agent, or Firm*—Chernoff, Vilhauer, McClung & Stenzel, LLP (57) ABSTRACT

An adhesively attachable bandage for an open wound. A one-way valve permits air or other fluids to move through the bandage in one direction, as to escape from a body cavity, but prevents fluids from moving in the other direction, as in entering the wound. A selectively sealable port can be opened to give access directly to the wound. The bandage may be transparent.

30 Claims, 4 Drawing Sheets

MEDICAL DRESSING FOR OPEN CHEST WOUNDS

The present invention relates to a medical dressing, in particular, but not exclusively, the invention relates to a medical dressing for treating open chest wounds and other similar injuries.

An open pneumothorax occurs when air is able to enter the chest cavity surrounding the lungs through an open chest wound, such as may be sustained as a result of being stabbed or shot. The admission of air into the chest cavity through a wound in this manner inhibits the normal breathing process and so can be life threatening.

Standard treatment for an open pneumothorax is to cover the wound with an occlusive dressing which is taped to the patient's skin along all four sides so as to seal the wound and prevent air from entering the chest cavity through the wound. If the wound is effectively sealed then normal breathing can be restored. However, if the seal is not perfect, more air may be drawn into and trapped in the chest cavity causing an increase in pressure inside the chest cavity. This is known as a tension pneumothorax and is a potentially more serious condition which can quickly lead to respiratory and heart failure.

Tension pneumothorax can also occur if the patient has suffered a punctured lung, as air can escape through the puncture into the chest cavity each time the patient breaths. If the open chest wound has been sealed, the air entering the chest cavity through the lung puncture is trapped and the pressure inside the chest cavity rises forcing the lung to collapse. Once the lung has collapsed, the pressure in the chest cavity will increase further so that the collapsed lung is pressed against the heart and the other lung. The blood flow from the heart to the lungs may be stopped if the pressure in the chest cavity increases above normal blood pressure.

Treatment of a tension pneumothorax with an open wound typically comprises using an occlusive dressing which is taped along only three sides so that pressurised air in the chest cavity can escape through the open side. However, the conditions in which such wounds are typically first treated make the successful application of this type of dressing difficult to achieve in practice.

Patients with an open chest wound will often also suffer a hemothorax or bleeding into the chest cavity. The build up of blood in the chest cavity inhibits normal lung expansion so that less air is inhaled and the level of oxygen in the blood is reduced. A hemothorax is often treated by inserting a chest tube through the wound and removing the blood from the chest cavity through the tube using suction. As this is an invasive procedure, it is usually carried out in a hospital rather than at the scene of an accident or in a battlefield situation. The treatment also requires access to the wound which is not possible whilst an occlusive dressing is in place.

U.S. Pat. No. 5,160,322 entitled "Occlusive Chest Sealing Valve" issued to Scheremet et al. on Nov. 3, 1992 discloses a one-way valve for use in the emergency closing of an open chest wound. The device comprises a one way valve assembly mounted to a flexible attachment panel having adhesive on one side so that it can be adhered to the skin of a patient over an open wound. The panel has an opening in the centre and the valve assembly has a base which is mounted to the panel so as to overlie the opening. There are a number of holes through the base and a valve member is mounted to the base which allows air and other fluids to pass out of the wound through the holes in the base but which prevents air being drawn back in. A dome shaped rigid cover is mounted to the base to cover the valve member and a number of openings are formed around the lower edge of the cover to enable air and other fluids exiting the wound to pass out of the cover.

The Scheremet valve is designed to prevent air being drawn into the chest cavity through an open wound whilst permitting pressurised air and other fluids, such as blood, to pass out through the valve to relieve a tension pneumothorax or preventing one from developing in the first place. However, it is a significant disadvantage of the Scheremet valve that it prevents access to the wound by medical personnel. Thus, if the patient has a hemothorax, blood may build up inside the chest cavity or a blood clot could develop at the wound site, clogging or blocking the valve. In this circumstance, the blood clot could not be removed from the wound site without removing the valve.

An attempt to overcome the drawbacks of the Scheremet valve and other similar devices is disclosed in U.S. Pat. No. 5,478,333 entitled "Medical Dressing for Treating Open Chest Injuries" issued to Asherman on Dec. 26, 1995. The Asherman dressing comprises a flexible body with adhesive on one side for attaching the body to the skin of a patient about an open chest wound. The centre of the body is formed into a flexible tubular duct which projects away from the patient. A flexible one-way valve tubing is mounted to the exterior of the duct to enable air and other fluids to pass out of the wound through the duct but which prevents air from being drawn back into the wound through the duct. If the patient has a hemothorax or collapsed lung, a suction device can be inserted into the flexible valve tubing and duct.

There are a number of drawbacks to the Asherman dressing. The Asherman dressing uses an acrylic adhesive and there have been reported problems in adhering the dressing to a patient's skin. In many cases where emergency treatment of an open wound is required, the patient's skin will be covered in blood, sweat and/or oil and the skin may also be covered in hair, all of which present difficulties when trying to adhere a dressing to the skin. Furthermore, because the duct and valve are flexible, medical personnel have to be careful to ensure that it does not collapse preventing proper operation of the valve. For example, medical personnel have to ensure that nothing contacts the duct or valve to cause it to collapse. This may be difficult depending on the location of the wound and the need to cover the patient in a blanket or to restrain the patient in a stretcher or other means for transporting the patient. A further problem with the Asherman dressing is that it obscures the wound from the view of medical personnel making assessment of the wound and the patient's condition difficult.

There is a need, therefore, for an improved medical dressing for an open chest wound which overcomes or at least mitigates the problems of the prior art arrangements.

In particular, there is a need for an improved medical dressing having a one-way valve means for occluding an open chest wound whilst permitting pressurised air and/or other fluids to pass out of the chest cavity and which permits access to the wound for inspection and/or to enable air and/or other fluids, such as blood, to be drawn from the wound whilst the dressing is in situ.

There is also a need for an improved medical dressing having a one-way valve means for occluding an open chest wound whilst permitting pressurised air and/or other fluids to pass out of the chest cavity through the wound which requires less monitoring than the prior art arrangements.

There is a further need for an improved medical dressing having a one-way valve means for occluding an open chest wound whilst permitting pressurised air and/or other fluids to pass out of the chest cavity which is easier to adhere to the skin of a patient than the prior art.

In accordance with a first aspect of the invention, there is provided a medical dressing for mounting over a wound in a patient, the dressing comprising:

a flexible panel having an inner surface and an outer surface and defining an opening therethrough, the panel having adhesive on the inner surface for attaching the panel to the skin of the patient;

a one-way valve assembly mounted to the panel across the opening in the panel, the valve assembly having a valve body defining a first passage through the body, the assembly further comprising a valve member configured to permit air and/or other fluids to flow through the first passage in an outward direction of the valve only so that, in use, air and/or other fluids are able to exit the wound through the first passage but are prevented from entering the wound through the first passage, the valve body further defining a second passage through the body, the valve assembly comprising a removable closure member for selectively closing the second passage to prevent fluid flow through the second passage.

In a medical dressing in accordance with the first aspect of the invention, the closure member can be removed to allow direct access to the wound through the second passage which is unobstructed by the valve member. Thus, the second passage can be opened up to enable medical personnel to inspect the wound and/or to carry out invasive procedures without having to remove the dressing. When the closure member is in position, the second passage is sealed and the dressing acts as an occlusive dressing which prevents air from entering the wound but which permits pressurised air and/or other fluids to exit the wound through the first passage.

The first and second passages may extend through the valve body from an inner side, which is configured to be positioned proximal to and adjacent the wound site, and an outer side, which is configured to be more distal from the wound site.

The second passage may extend through a central region of the valve body and the first passage may substantially surround the second passage.

The valve body may include a valve base and a valve cover mounted to the valve base, the valve member being mounted to the valve base and encased by the valve cover.

The valve base may have an inner surface and an outer surface and may define at least one valve opening through the base, the valve member being mounted to the base for movement between a valve closed position, in which the valve member contacts the outer surface of the base so as to prevent air and/or other fluids flowing inwardly through said at least one valve opening, and a valve open position, in which the valve member is at least partially spaced from the outer surface of the base member so that that air and/or other fluids can pass through said at least one valve opening in an outward direction of the valve assembly.

The valve base may define a further opening through the base, which further opening comprises at least a part of the second passage, the further opening being unobstructed by the valve member.

The further opening comprising at least part of the second passage may be defined substantially centrally in the valve base and the valve base may further define two or more valve openings comprising part of the first passage which are circumferentially spaced about the further opening.

The at least one valve opening and the further opening may be defined in a generally central region of the base and the valve base may further comprise an outer flange portion surrounding the central region.

In one embodiment, the generally central portion of the base has a substantially flat outer surface and the valve member is flexible. Where the further opening in the base is positioned centrally, the valve member may be annular.

In an alternative embodiment, the generally central portion of the valve base comprises a frusto-conical portion which projects outwardly and said at least one valve opening is formed in the frusto-conical portion. In this embodiment, the further opening in the base may extend centrally through the apex of the frusto-conical portion.

Where the generally central portion of the base comprises a frusto-conical portion, the valve member may comprise a frusto-conical wall portion and may be movable between a valve closed position, in which an inner surface of the frusto-conical wall portion of the valve member abuts an outer surface of the frusto-conical portion of the base, and an open position, in which the inner surface of the frusto-conical wall portion of the valve member is spaced from the outer surface of the frusto-conical portion of the base. The valve member may be rigid.

The valve cover may comprise a housing portion which encases the valve member.

The valve cover may have an inner surface and an outer surface and may define at least one valve outlet opening through the housing portion of the cover, wherein said at least one valve outlet opening forms part of the first passage.

The cover may also define a further opening through the housing portion of the cover which aligns with the further opening in the base to form at least part of the second passage.

An annular projection may be provided on an inner surface of the cover surrounding the further opening therein and a corresponding annular projection may be provided on the outer surface of the base surrounding the further opening in the base, the corresponding annular projections mutually engaging to define the second passage.

The annular projection on the cover may be an inwardly projecting hollow spigot and the annular projection on the base may be a stepped lip, an axial free end of the spigot having a recess which receives part of the stepped lip.

The first passage may be defined by said at least one valve opening in the valve base, the volume between the valve cover and the valve base surrounding the corresponding annular projections and said at least one valve outlet opening in the cover.

The valve cover may have an outer flange portion which overlies a flange portion of the valve base, a portion of the panel surrounding the opening therein being sandwiched between the flange portions.

Each of the panel, the valve base, the valve cover, and the valve member may be transparent or translucent.

The adhesive on the inner surface of the panel may comprise a hydrogel or hydrocolloid adhesive.

A layer of one type of adhesive, such as a hydrogel or hydrocolloid may be applied to a major central portion of the inner surface of the panel and a thinner layer of a second adhesive, such as an acrylic adhesive, may be applied to a peripheral border of the inner surface surrounding the central portion.

The valve may be configured for mounting about an open chest wound.

In accordance with a second aspect of the invention, there is provided a medical dressing comprising:

a flexible panel having an inner surface and an outer surface and defining an opening therethrough, the panel having adhesive on the inner surface for attaching the panel to the skin of a patient;

a one-way valve assembly mounted to the panel across the opening in the panel, the valve assembly comprising:

a valve base having a central opening through the base and a plurality of valve openings through the base spaced circumferentially about the central opening;

an annular valve member mounted to the base member about the central opening so as to overlie the valve openings at least when the valve is closed, the valve member being configured so as to permit air and/or other fluids to flow outwardly through the valve openings whilst preventing air and/or other fluids from flowing inwardly through the valve openings;

a valve housing mounted to the valve base so as to encase the valve member, the valve housing having a central opening in alignment with the central opening in the base and a plurality of valve outlet openings circumferentially spaced about the central opening, the valve assembly may further comprise means extending between the central opening in the base and the central opening in the cover to define a continuous, fluid tight central passage through the valve assembly;

a removable closure member for selectively closing the central passage.

In accordance with third aspect of the invention, there is provided a medical dressing, the dressing comprising:

a flexible panel having an inner surface and an outer surface and defining an opening therethrough, the panel having adhesive on the inner surface for attaching the panel to the skin of the patient;

a one-way valve assembly mounted to the panel to control the flow of fluid through the opening; the valve assembly comprising:

a valve base having a central portion and an outer flange portion, the base defining at least one valve opening through the central portion of the base, the central portion of the base extending through the opening of the panel with the flange portion abutting the inner surface of the panel about the opening in the panel;

a valve member mounted to the valve base to regulate the flow of air and/or other fluids through the at least one valve opening, the valve member being configured so as to permit air and/or other fluids to flow outwardly through the at least one valve opening whilst preventing air and/or other fluids from flowing inwardly through the at least one valve opening;

a valve cover mounted to the valve base, the cover comprising a housing portion in which the central portion of the valve base is received and an outer flange portion which opposes the flange portion on the base and which abuts the outer surface of the panel about the opening in the panel, the housing portion having at least one valve outlet opening therein through which air and/or fluid flowing outwardly through the at least one valve opening in the base can pass to exit the valve assembly in use;

the valve base and the valve cover defining a further passage through the valve assembly which further passage opens through the central portion of the valve base, the further passage being fluidly isolated from the remainder of the valve assembly and unobstructed by the valve means;

the valve assembly also comprising a removable closure member for selectively closing the further passage.

Several embodiments of the invention will now be described, by way of example only, with reference to the accompanying drawings, in which.

With reference to FIGS. 1 to 4, a first embodiment of a medical dressing 10 in accordance with the invention comprises a flexible panel 12 and a valve assembly 14 mounted to the panel.

Figure 1:
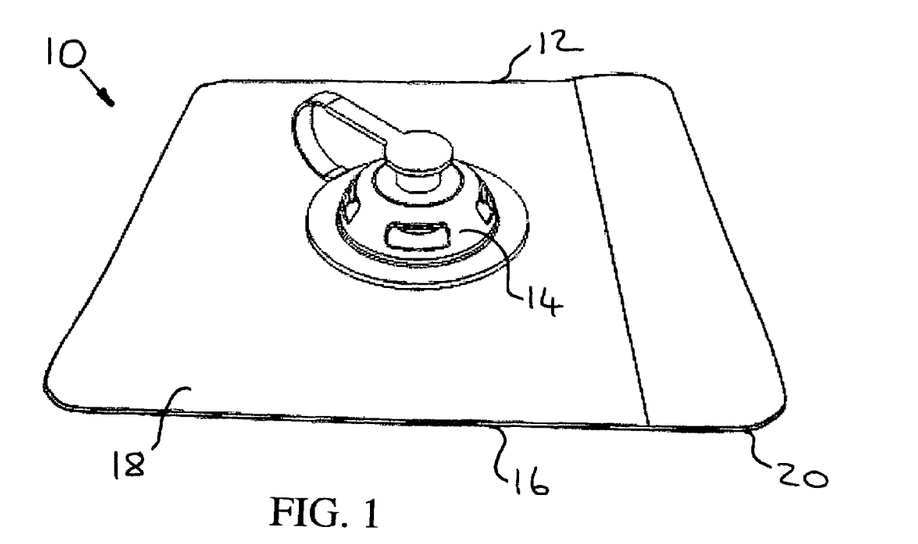
FIG. 1 is a perspective view of a first embodiment of a medical dressing in accordance with the invention.

The panel 12 is in the form of a thin sheet of flexible material that in the present embodiment is generally square in shape. It will be appreciated that the actual shape of the panel is not essential to the invention and that the panel can be formed in any suitable shape and could be rectangular or circular for example. The panel 12 can be made of any suitable material which occludes the wound. For example, the panel 12 can be made from a non-woven film of polyurethane, polyurethane foam or polyethylene foam. The panel is preferably made of a transparent or at least translucent material but this is not essential.

The panel 12 has an inner surface 16 and an outer surface 18. The inner surface 16 is coated with an adhesive to enable the panel to be adhered to the skin of a patient about an open chest wound. When the dressing is applied, it is likely that the patient's skin in the region of the wound will be covered in blood, sweat and other contaminants such as oil and the like and may also be covered in hair. The skin surrounding the wound should be cleaned prior to applying the dressing 10 but this may not be totally effective, particularly if the dressing 10 is being applied in battlefield conditions. It is important, therefore, that the adhesive used enables the panel to be firmly attached all the way around the wound, even where the skin is not thoroughly cleaned.

Any suitable adhesive can be used but the adhesive will typically be a pressure sensitive adhesive that is transparent or translucent. The adhesive may be an acrylic adhesive but is preferably an aggressive hydrogel or hydrocolloid, both of which have a good wet tack and so are able to adhere to damp skin and retain their tackiness over time. A relatively thick layer of one type of adhesive, such as an aggressive hydrogel or hydrocolloid adhesive, may be applied over the whole inner surface 16 surrounding the valve 14 so that the panel has a uniform thickness. Alternatively, a relatively thick layer of a first adhesive, such as a hydrogel or hydrocolloid, can be applied to the major central portion of the surface 16 of the panel about the valve 14, while a thinner layer of a second adhesive, such as an acrylic adhesive, is applied to a peripheral border of the surface 16. This results in a panel which when adhered to the skin presents a lower profile at the edges and therefore would be less likely to roll up and detach from the skin. The border may extend inwardly for about 5 to 10 mm around the outer perimeter edge of the panel.

The panel 12 has an opening 12a, which is preferably located centrally of the panel, and the valve assembly 14 is mounted to the panel 12 across the opening 12a. In use, the panel 12 is attached to the patient's skin so that the valve assembly 14 is positioned centrally over the wound, with the panel being stuck to and sealing with the skin surrounding the wound so that air and/or other fluids such as blood are only able to pass into and out of the wound through the valve assembly.

The dressing 10 will usually be supplied with a non-stick protective backing (not shown) which covers the adhesive and which can be peeled away when the dressing is applied. A strip 20 of a further non-stick protective material is positioned on the inner surface 16 along one edge of the panel so that the panel can be grasped along that edge to remove it from the protective backing and to position it about the wound. This further strip of material 20 is peeled away once the panel is correctly located so that the region of the panel covered by strip can also be adhered to the patient's skin.

Figure 2:
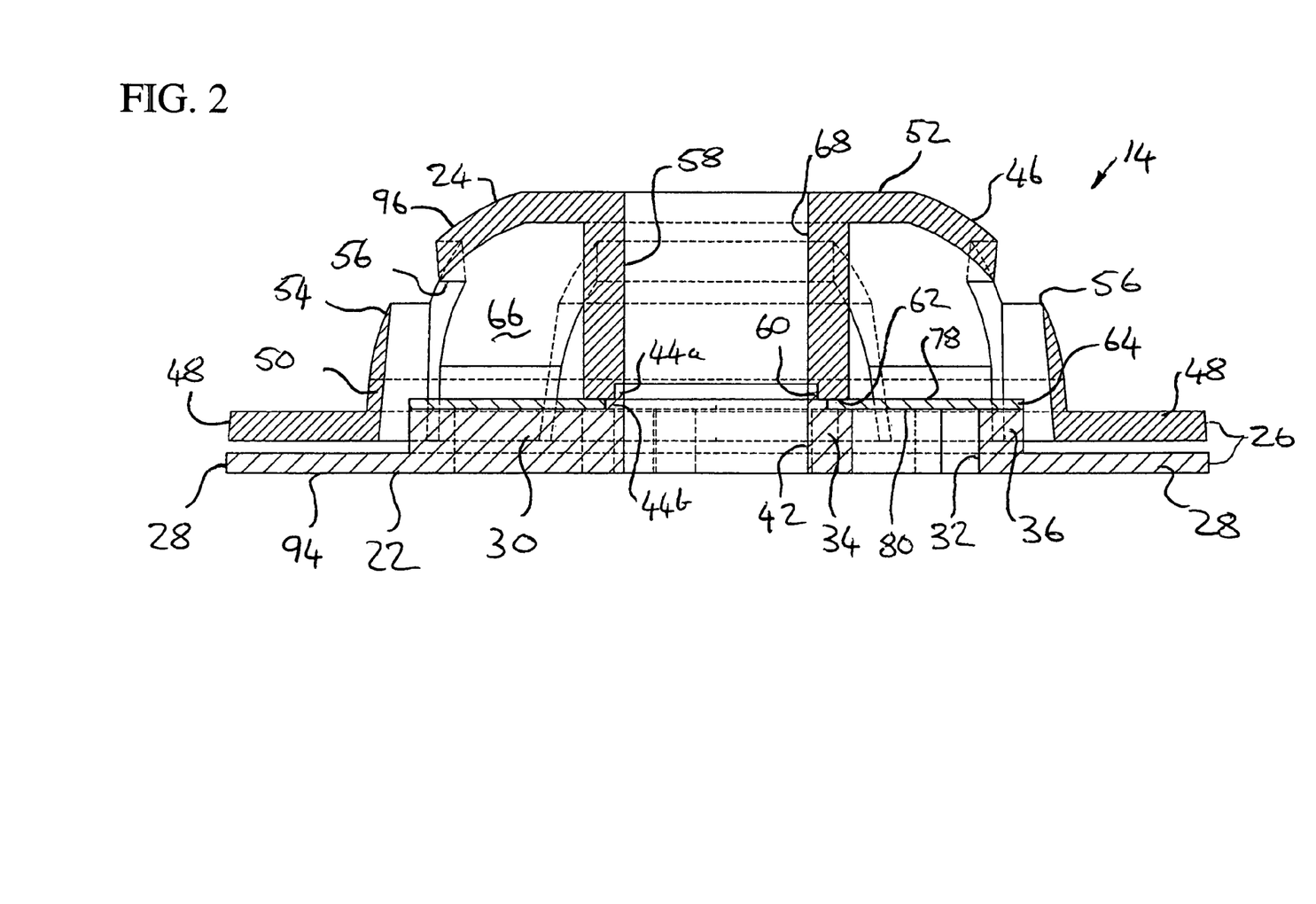
FIG. 2 is a cross sectional view through a valve assembly forming part of the medical dressing of FIG. 1, shown on an enlarged scale.
Figure 3:
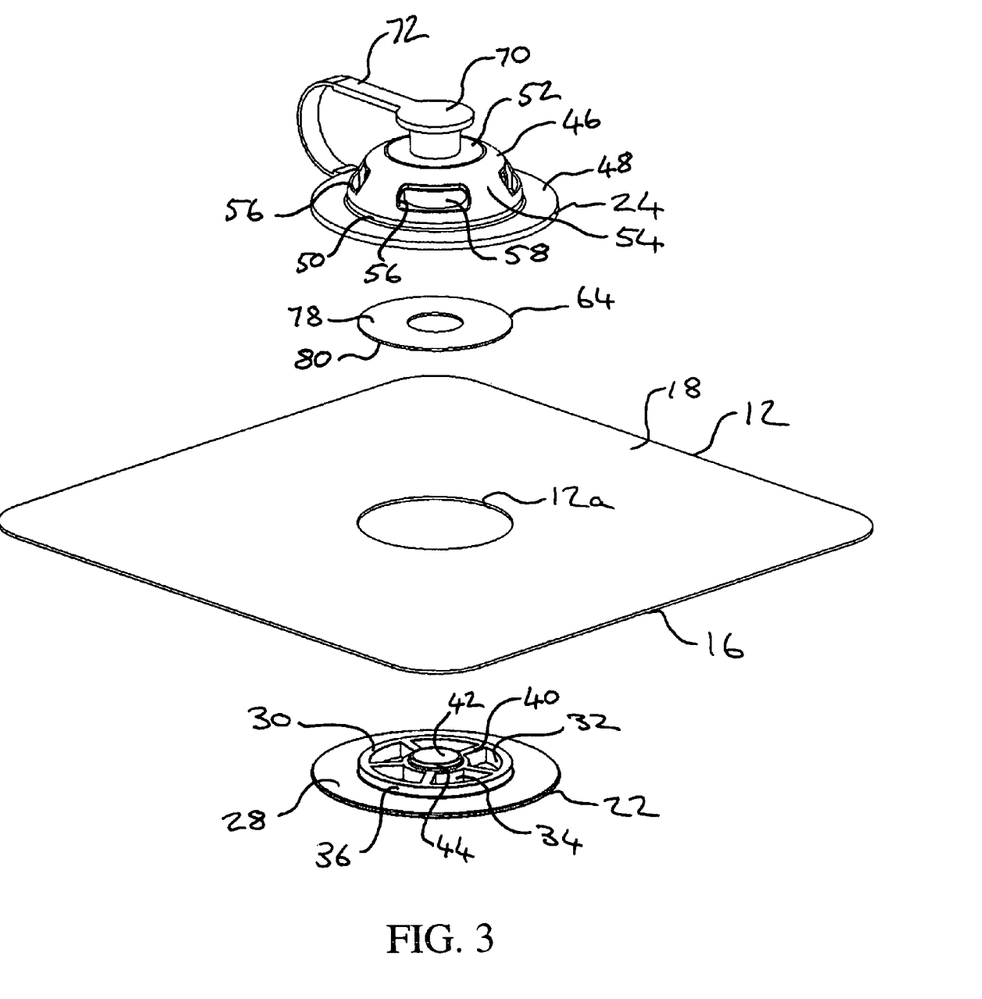
FIG. 3 is an exploded view of the medical dressing of FIG. 1.
Figure 4:
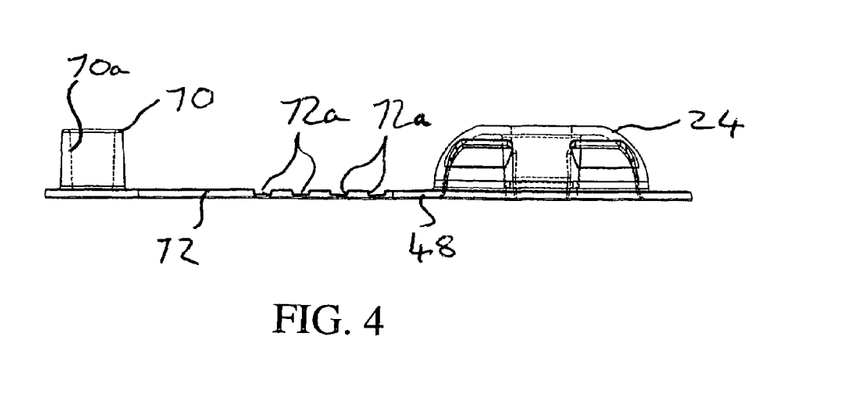
FIG. 4 is a side elevation of a cover member forming part of a valve assembly of the medical dressing of FIG. 1.

The valve assembly 14 can be seen best in FIGS. 2 to 4 and includes a valve base 22 and a valve cover 24 which together comprise a valve body, indicated generally at 26.

The base 22 is a generally disc shaped member having a relatively thin annular flange portion 28 surrounding a thicker central portion 30. Five arcuate valve openings 32 are formed through the central portion 30 dividing the central portion into an inner ring 34 and an outer ring 36. The arcuate valve openings 32 are spaced circumferentially about the central portion and are separated by radial spokes 40 which connect the inner and outer rings 34, 36. A bore 42 extends through the inner ring 34 and forms a further opening through the central portion 30. A stepped annular lip 44 projects outwardly, that is to say away from the wound site in use, from a radially inner edge of the outer surface of the inner ring 34 for reasons that will be discussed below.

The valve cover 24 is circular in plan view having an inner domed housing portion 46 and an outer annular flange portion 48 that extends radially outwardly about the periphery of the domed portion 46. The domed portion 46 has a flat annular wall region 50 at its base, a flattened upper surface 52 and a generally curved wall portion 54 between the flat annular wall region 50 and the upper surface. A series of openings 56 are spaced circumferentially about the curved wall portion 54. The openings 56 form a fluid outlet of the valve assembly as will be described in more detail later.

The inner diameter of the annular wall region 50 is slightly larger than the outer diameter of the raised central portion 30 of the valve base 22, so that the central portion 30 of the base 22 is received within the domed portion 46 of the cover 24 when the cover and base are assembled together. A hollow spigot 58 projects inwardly from the centre of the flattened upper surface 52 for engagement with the stepped lip 44 on the valve base. An annular recess 60 is formed about the inner surface of the free end of the spigot 58 into which an outer portion 44a of the stepped lip locates with an interference or snap fit to hold the cover 24 and the base 22 together. When the base 22 and cover are assembled, the free axial end surface 62 of the spigot 58 abuts the inner portion 44b of the stepped lip and the flange portion 48 of the cover 24 overlies the flange portion 28 of the base 22.

The valve base 22 and the valve cover 24 are both made from a generally rigid material, such as a rigid polymeric material. Preferably, the valve base 22 and the valve cover 24 are made from a transparent or translucent polymeric material, such as polypropylene, acetyl or any other suitable material, and may be manufactured by means of injection moulding for example.

A flat annular valve member 64 is mounted to the central portion 30 of the valve base 22 about the lip 44. The valve member 64 has an outer diameter which is coincides with the outer diameter of the raised central portion 30 of the base and an inner diameter which is slightly larger than the inner portion 44b of the lip, so that the valve member covers the whole of the valve openings 32 as well as at least a portion of each of the inner and outer rings 34, 36. In the present embodiment, when the cover 24 is assembled to the base 22, the axial free end 62 of the central spigot 58 on the cover overlies an inner diameter portion of the valve member 64 to hold it in position against the inner ring 34 of the base. However, in an alternative arrangement, the inner diameter of the valve member may be slightly larger than the outer diameter of the spigot 58 so that the valve member is able to slide along the outer surface of the spigot 58. The valve member 64 is made of a flexible material, such as a flexible polymer (e.g. silicon) which preferably is transparent or at least translucent.

To mount the valve assembly 14 to the panel 12, a region of the panel 12 surrounding the central opening 12a is clamped between the annular flange portions 28, 48 of the base 22 and the cover 24. During assembly of the dressing 10, the raised central portion 30 of the base 22 is inserted through the opening 12a in the panel so that a region of the panel surrounding the opening 12a is positioned over the annular flange portion 28 of the base. With the flexible valve member 64 in position on the central raised portion 30 of the base 22, the valve cover 24 is assembled to the base 22 so that the recess 60 in the spigot 58 engages the annular lip 44 and the region of the panel 12 surrounding the central opening 12a is clamped between the annular flange portion 48 of the cover 24 and the annular flange portion 28 of the base. The cover 24 and base 22 may be held together solely by the frictional engagement of the lip 44 in the recess 60 or they may be adhered together using a suitable adhesive or welded together for example by means of ultrasonic welding. Adhesive may also be used to bond the annular flange portions 28, 48 of the base and cover to the panel 12 to ensure that an air-tight seal is formed between the panel and the flange portions.

Where the base 22 and cover 24 are bonded together using adhesive or ultrasonic welding, the recess 60 and the stepped lip 44 could be omitted and the inner end of the spigot 58 may have a flat surface with abuts a correspondingly flat surface on the cover about the central bore 42.

With the dressing 10 assembled as described above, the arcuate openings 32 in the base 22, the volume between the base 22 and the inner surface of the cover 24 surrounding the central spigot 58, and the openings 56 in the curved wall portion of the cover form a first passage 66 extending through the valve body and through which air and/or other fluids can flow under the control of the valve member 64.

The diameter of bore 42 in the inner ring and the inner diameter of the hollow spigot 58 are substantially the same so that when the base 22 and cover 24 are assembled, the inner ring 34 and the hollow spigot 58 define a continuous second passage 68 extending through the centre of the valve body 26. The connection between the spigot 58 and the lip 44 on the inner ring 34 is such as to prevent air and/or other fluids from seeping between the join so that the second passage 68 is fluidly isolated from the first passage. 66. The second passage 68 is unobstructed by the valve member 64.

The valve assembly also includes a closure member 70 for the second passage which is shown only in FIGS. 1, 3 and 4. The closure member 70 comprises a plastics bung which can be removably inserted into the bore of the hollow spigot 58 to seal the second passage 68 against the flow of air and/or other fluids. The bung 70 is preferably attached to the cover by means of a flexible strip of material 72 which forms a lanyard. In the present embodiment, the lanyard 72 and the bung 70 are formed integrally with the cover 24 and the lanyard projects from an outer edge of the flange portion 48 of the cover. As can be seen in FIG. 4, the lanyard is formed with a series of grooves 72a extending across its width which helps the lanyard to flex. The bung 70 is hollow having an annular wall portion 70a which defines a blind bore. The annular wall portion 70a is resiliently compressed when the bung is inserted in the spigot 58 so that it forms an effective seal to prevent air and/or other fluids passing through the second passage. The lanyard 72 enables the bung 70 to be removed from the second passage whilst remaining connected to the cover 24 as shown in FIG. 4.

Preferably, the bung 70, lanyard 72 and cover 24 are formed integrally as an injection moulding. However, the bung 70 and lanyard 72 could be formed separately from the cover 24 with an end of the lanyard secured to the cover by any suitable means. For example, a free end of the lanyard 72 could be inserted through an opening or slot in the cover and have flexible projections which are arranged so that it can be inserted through the opening or slot in one direction but cannot be easily withdrawn from the opening or slot in the opposite direction. It will be appreciated that other methods of attaching the lanyard 72 to the cover 24 can be used.

In use, the dressing 10 is attached to a patient having an open chest wound with the valve assembly 14 positioned directly over the wound and the inner surface 16 of the panel 12 stuck to the patient's skin around the wound to form an air tight seal. With the dressing in position and the closure member 70 located in the bore of the hollow spigot 58, air and/or other fluids are only able to pass out of the wound through the first passage 66 under the control of the valve member 64. When the pressure of the ambient air acting on an outer surface 78 of the valve member 64 is greater than the pressure of the air and/or other fluids, such as blood, in the chest cavity acting on an inner surface 80 of the valve member 64, the valve member is pressed against the outer face of the raised central portion 30 of the valve base 22 closing the arcuate openings 32 and preventing air from being drawn into the chest cavity through the valve assembly and the wound. However, should the pressure of the air and/or other fluids in the chest cavity exceed the ambient air pressure, the flexible valve member 64 is at least partially lifted away from the outer surface of the central raised portion 30 of the valve base. This permits the pressurised air and/or other fluids in the chest cavity to flow outwardly through the arcuate openings 32 in the valve base, through the space between the valve base and the inner surface of the valve cover 24 surrounding the central spigot 58 and out through the openings 56 in the curved wall portion of the valve cover. The ability for pressurised air and/or blood to escape from the chest cavity through the first passage 68 in the valve assembly helps in treating, and in certain circumstances preventing the occurrence of, a tension pneumothorax and/or a hemthorax.

As described above, with the second passage 68 in the valve body closed, a medical dressing 10 in accordance with the invention acts as a one-way valve to prevent air from being drawn into the chest cavity through the wound whilst permitting pressurised air, blood, and/or other fluids, to flow out of the chest cavity. However, by removing the closure member 70, direct access to the wound can be provided via the second passage 68 without the need to remove the dressing 10. The open second passage 68 can be used to perform a visual inspection of the wound and/or to enable invasive procedures to be carried through the passage without the need to remove the dressing 10. For example, a chest drain can be introduced into the chest cavity through the second passage in order to suction blood or other fluids from the chest cavity in the event of the patient suffering a hemothorax or to suction air from the chest cavity in the event of a tension pneumothorax. Should the first passage 66 become clogged with clotted blood, suctioning through the second passage 68 can be used to remove the clot and restore air and fluid flow through the first passage 66.

The panel 12, and the various components of the valve assembly 14 are preferably all manufactured from transparent or at least translucent materials in order to aid the user in placing the dressing 10 accurately with the valve assembly positioned centrally over the wound. The transparent nature of the dressing also makes it easier to monitor the wound visually.

The rigid cover portion 14 of the valve assembly protects the valve member 64 and will not easily collapse in the manner of the flexible duct and valve member of the prior art Asherman dressing. As a result, the dressing 10 in accordance with the invention requires less monitoring and attention by medical personnel.

Figure 5:
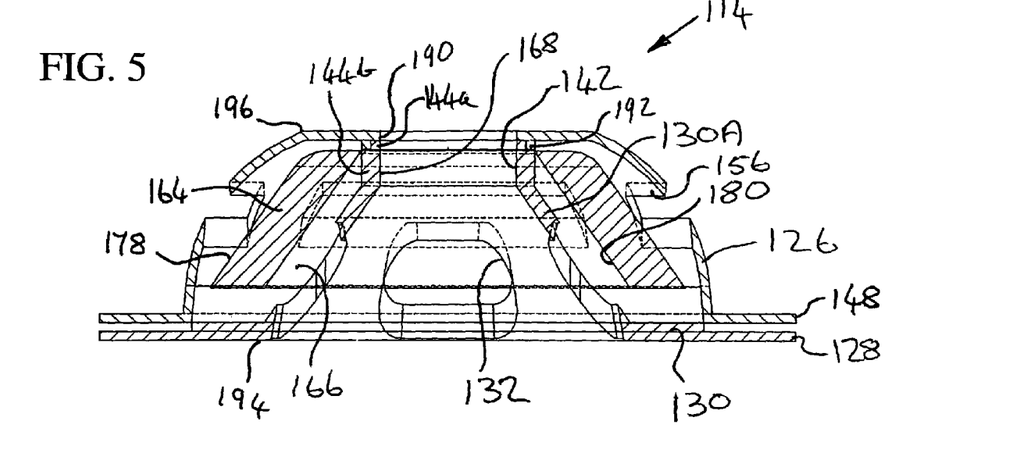
FIG. 5 is an enlarged cross sectional view similar to that of FIG. 2, but on a slightly smaller scale, of a second embodiment of a valve assembly for use with a medical dressing in accordance with the invention.
Figure 6:
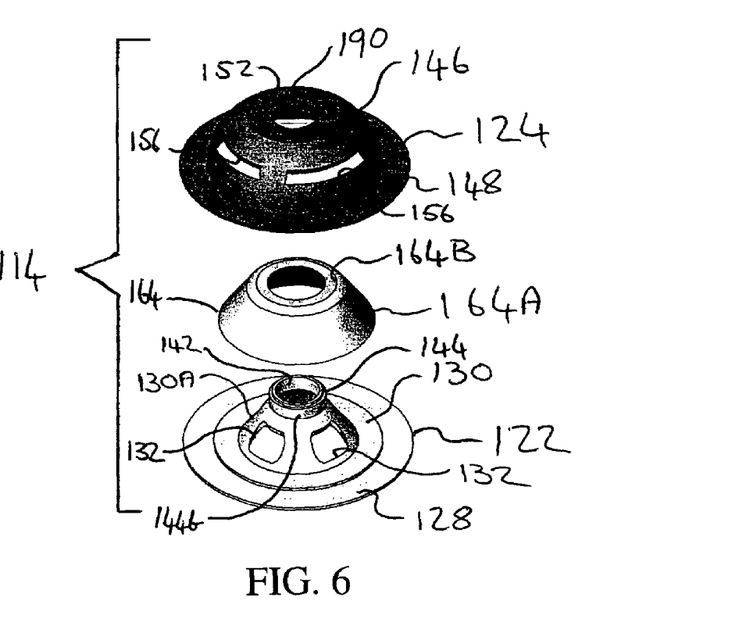
FIG. 6 is an exploded view of the valve assembly of FIG. 5.

FIGS. 5 and 6 illustrate an alternative embodiment of a valve assembly 114 which can be used with a dressing 10 in accordance with the invention.

In the following description, the same reference numerals but increased by 100 will be used to denote the same or equivalent features to those of the first embodiment as described above with reference to FIGS. 1 to 4.

The valve assembly 114 of the second embodiment is similar in construction and operation to that of the first embodiment and comprises a valve base 122 and a valve cover 124 (which together define a valve body 126) and a valve member 164.

The valve base 122, comprises an outer annular flange portion 128 and a central portion 130 of increased thickness. The central portion 130 in this embodiment comprises a frusto-conical wall portion 130A which extends outwardly of the base, i.e. away from the wound site in use. A series of circumferentially spaced openings 132 are formed through the frusto-conical wall portion 130A to provide an inlet to the first fluid passage 166 of the valve assembly 114.

An extended, stepped annular lip 144 is provided at the radially inner, or upper as shown, edge of the frusto-conical wall portion 130A and comprises an outer portion 144a of smaller diameter and an inner portion 144b of larger diameter. The inner portion 114b in this embodiment is of an increased length when compared that of the lip 44 in the first embodiment. The lip 144 defines a central bore or opening 142 through the base and which opens into the interior of the frusto-conical wall portion 130A.

The valve cover 124 in the second embodiment is similar to the valve cover 24 in the first embodiment and has a domed portion 146 and an annular flange portion 148 projecting radially outwardly about the periphery of the domed portion. However, the cover 124 in the second embodiment does not have a hollow spigot 58 but rather has a circular opening 190 in the centre of the flattened upper surface 152. The opening 190 is substantially the same diameter as the bore 142 through the lip 144 of the base 122. An annular flange 192 projects inwardly from an inner surface of the cover. The flange 192 is spaced from the opening 190 in the cover and is configured for engagement with the stepped lip 144 on the base, as shown in FIG. 5. Thus in the second embodiment, the bore 142 defined by the lip 144 in the base 122 and the opening 190 in the cover together define a second passage 168 through the valve body.

The valve member 164 is rigid and may be made of any suitable material such as a rigid polymeric material. The valve member 164 has a frusto-conical portion 164A which corresponds with the frusto-conical wall portion 130A on the base. An annular wall region 164B protects radially inwardly from the outer (or upper as shown) end of the frusto-conical portion 164A for sliding engagement about the extended inner portion 144b of the lip 144. The arrangement is such that the valve member 164 is able to move in an axial direction of the valve assembly between a valve open position, as shown in FIG. 5, and a valve closed position.

In the valve open position, the annular wall region 164B of the valve member is located towards the outer (or upper as shown) end of the extended inner lip portion 144b and the inner surface 180 of the frusto-conical portion 164A of the valve member 164 is spaced from the frusto-conical wall portion 130A of the base. With the valve member 164 in this position, air and/or other fluids are able pass through the openings 132 in the base, the space between the base 122 and the inner surface of the cover 114 and out through the openings 156 in the cover. In the valve closed position, the valve member 164 slides inwardly, towards the wound site, so that the inner surface 180 of its frusto-conical portion is in contact with the outer surface of the frusto-conical wall portion 130A of the base. In this position, the valve member closes the openings 132 in the base to prevent air and/or other fluids flowing through the openings 132 in an inward direction.

Although not shown in the drawings, the valve assembly 114 has a removable closure member similar to the closure member 70 in first embodiment that can be inserted into the opening 190 in the cover and/or the bore 142 in the base to close the second passage.

In use, when the second passage 168 is closed by the closure member, the valve member 164 is moved in response to the pressure differential across the valve member. If the pressure of the air and/or other fluids in the chest cavity acting on the inner surface 180 of the valve member through the openings 132 in the base is higher that the ambient air pressure acting on the outer surface 178 of the valve member, the valve member 164 will move to the valve open position to permit the pressurised air and/or other fluids to flow outwardly through the valve body. However, if the ambient air pressure is higher than the pressure of the air and/or other fluids in the chest cavity, the valve member 164 is held in the valve closed position, preventing air being drawn into the chest cavity through the first passage 166. As with the first embodiment, the closure member for the second fluid passage 168 can be removed to provide direct access to the chest wound through the unobstructed second passage.

The valve assembly 114 of the second embodiment can be mounted to a panel 12 in a manner similar to that described above in relation to the first embodiment. Thus, the central portion 130 of the base is inserted through the opening 12a in the panel, and the valve member 164 and cover are mounted to the base so that a region of the panel surrounding the opening 12a is sandwiched between the flange portions 128, 148 of the base 122 and the cover 124 respectively.

In both embodiments of the inventive dressing 10, the valve body 26, 126 defines two separate passages 66, 68; 166, 168 that extend through the body from an inner side 94, 194, which is located proximal to and adjacent the wound in use, to an outer side 96, 196, which is located more distal from the wound in use. The valve member 64, 164 is operative in the first of the passages so that air and/or other fluids may only pass through the first passage 66, 166 in an outward direction from the inner side to the outer side. The second passage 68, 168 is unobstructed and allows direct access to wound in use but may be sealed by the closure member 70 when direct access is not required. When the second passage is sealed, the dressing occludes the wound to prevent air being drawn into the chest cavity through the wound whilst permitting pressurised air and/or other fluids to escape from the chest cavity through the first passage. It can be seen, therefore, that a medical dressing 10 in accordance with the invention provides an effective and easy to use dressing for an open chest wound that is simple in design and reliable in operation.

Whilst the dressing is particularly advantageous in treating open chest wounds it may have other applications. For example, the dressing may be useful in attaching a drain to a patient whether in the chest cavity or elsewhere.

Whereas the invention has been described in relation to what is presently considered to be the most practical and preferred embodiments, it is to be understood that the invention is not limited to the disclosed arrangements but rather is intended to cover various modifications and equivalent constructions included within the spirit and scope of the invention. For example, the second passage may be defined by means of a hollow spigot protecting outwardly from the base about a central opening, the spigot extending through an opening in the cover. Furthermore, it will be appreciated that whilst it is advantageous for the second passage to be formed in the centre of the valve assembly so that it can be positioned over the centre of the wound, this is not essential. The first and second passages could, for example be aligned side by side. It should also be understood that even where the second passage is positioned centrally of the valve assembly, this does not require the that the passage be formed in the exact geometric centre of the assembly provided the dressing can be positioned with the second passage aligned with the wound opening.

Where the terms "comprise", "comprises", "comprised" or "comprising" are used in this specification, they are to be interpreted as specifying the presence of the stated features, integers, steps or components referred to, but not to preclude the presence or addition of one or more other feature, integer, step, component or group thereof.

The invention claimed is:

1. A medical dressing for mounting over a wound in a patient, the dressing comprising:
   (a) a flexible panel having an inner surface and an outer surface and defining an opening therethrough, the panel having adhesive on the inner surface for attaching the panel to the skin of the patient; and
   (b) a one-way valve assembly mounted to the panel across the opening in the panel, the valve assembly having a valve body defining a first passage through the body, the assembly further comprising a valve member configured to permit air and or/other fluids to flow through the first passage in only an outward direction of the valve, so that, in use, air and/or other fluids are able to exit the wound through the first passage but are prevented from entering the wound through the first passage, the valve body further defining a second passage through the body, the valve assembly comprising a removable closure member for selectively closing the second passage to prevent fluid flow through the second passage.

2. A medical dressing as claimed in claim 1, in which the second passage is unobstructed when the closure member is removed so as to provide direct access to a wound covered by the dressing in use.

3. A medical dressing as claimed in claim 1, in which the first and second passages extend through the valve body between an inner side, which is configured to be positioned proximal to the wound in use, and an outer side, which is configured to be distal from the wound in use.

4. A medical dressing as claimed in claim 1, in which the second passage extends through a central region of the valve body and the first passage substantially surrounds the second passage.

5. A medical dressing as claimed in claim 1, in which the valve body comprises a valve base and a valve cover mounted to the valve base, the valve member being mounted to the valve base and encased by the valve cover.

6. A medical dressing as claimed in claim 5, in which the valve base has an inner surface which faces the wound site in use and an outer surface which faces away from the wound site in use, the valve base defining at least one valve opening through the base, the valve member being mounted to the base for movement between a valve closed position, in which the valve member contacts the outer surface of the base so as to prevent air and/or other fluids flowing inwardly through said at least one valve opening, and a valve open position, in which the valve member is at least partially spaced from the outer surface of the base member so that that air and/or other fluids can pass through said at least one valve opening in an outward direction of the valve assembly.

7. A medical dressing as claimed in claim 6, in which the valve base defines a further opening through the base, which further opening comprises at least a part of the second passage, the further opening being unobstructed by the valve member.

8. A medical dressing as claimed in claim 7, in which the further opening is defined substantially centrally of the valve base and the valve base defines at least two valve openings which are circumferentially spaced about the further opening.

9. A medical dressing as claimed in claim 8, in which the at least one valve opening and the further opening are defined in a central region of the base and the valve base further comprises an outer flange portion surrounding the central region and in which the valve member is annular.

10. A medical dressing as claimed in claim 6, in which the at least one valve opening and the further opening are defined in a central region of the base and the valve base further comprises an outer flange portion surrounding the central region.

11. A medical dressing as claimed in claim 10, in which the central portion of the base has a generally flat outer surface and the valve member is flexible.

12. A medical dressing as claimed in claim 10, in which the central portion of the valve base comprises a frusto-conical portion which projects outwardly and said at least one valve opening is formed in the frusto-conical portion.

13. A medical dressing as claimed in claim 12, in which the further opening in the base extends centrally through an apex of the frusto-conical portion.

14. A medical dressing as claimed in claim 12, in which the valve member comprises a frusto-conical wall portion and the valve member is movable between a valve closed position, in which an inner surface of the frusto-conical wall portion of the valve member abuts an outer surface of the frusto-conical portion of the base, and an open position, in which the inner surface of the frusto-conical wall portion of the valve member is spaced from the outer surface of the frusto-conical portion of the base.

15. A medical dressing as claimed in claim 14, in which the valve member is rigid.

16. A medical dressing as claimed in claim 10, in which the valve cover has an outer flange portion which overlies the flange portion of the valve base, a portion of the panel surrounding the opening therein being sandwiched between the flange portions.

17. A medical dressing as claimed in claim 5, in which the valve cover comprises a housing portion which encases the valve member.

18. A medical dressing as claimed in claim 17, in which the cover has an inner surface and an outer surface and defines at least one valve outlet opening through the housing portion of the cover, said at least one valve outlet opening forming part of the first passage.

19. A medical dressing as claimed in claim 18, in which the valve base has an inner surface which faces the wound site in use and an outer surface which faces away from the wound site in use, the valve base defining at least one valve opening through the base, the valve member being mounted to the base for movement between a valve closed position, in which the valve member contacts the outer surface of the base so as to prevent air and/or other fluids flowing inwardly through said at least one valve opening, and a valve open position, in which the valve member is at least partially spaced from the outer surface of the base member so that that air and/or other fluids can pass through said at least one valve opening in an outward direction of the valve assembly and in which the valve base defines a further opening through the base, which further opening comprises at least a part of the second passage, the further opening being unobstructed by the valve member and in which the cover defines a further opening through the housing portion of the cover, the further opening through the cover aligning with the further opening through the base to form at least part of the second passage.

20. A medical dressing as claimed in claim 19, in which an annular projection is provided on an inner surface of the cover surrounding the further opening therethrough and a corresponding annular projection is provided on the outer surface of the base surrounding the further opening through the base, the corresponding annular projections mutually engaging to define the second passage.

21. A medical dressing as claimed in claim 20, in which the annular projection on the cover is an inwardly projecting hollow spigot and the annular projection on the base is a stepped lip, an axial free end of the spigot having a recess which receives part of the stepped lip.

22. A medical dressing as claimed in claim 20, in which the first passage comprises the at least one valve opening through the valve base, a volume defined between the valve cover and the valve base surrounding the corresponding annular projections and the at least one valve outlet opening in the cover.

23. A medical dressing as claimed in claim 1, in which each of the panel, the valve body, the valve cover, and the valve member is transparent.

24. A medical dressing as claimed in claim 1, in which the adhesive on the inner surface of the panel comprises a hydrogel adhesive.

25. A medical dressing as claimed in claim 1, in which layer of one type of adhesive, such as a hydrogel or hydrocolloid is applied to a major central portion of the inner surface of the panel and a thinner layer of a second adhesive, such as an acrylic adhesive, is applied to a peripheral boarder of the inner surface surrounding the central portion.

26. A medical dressing as claimed in claim 1, in which the dressing is configured for mounting over an open chest wound in a patient.

27. A medical dressing as claimed in claim 1, in which each of the panel, the valve body, the valve cover, and the valve member is translucent.

28. A medical dressing as claimed in claim 1, in which the adhesive on the inner surface of the panel comprises a hydrocolloid adhesive.

29. A medical dressing comprising:
(a) a flexible panel having an inner surface and an outer surface and defining an opening therethrough, the panel having adhesive on the inner surface for attaching the panel to the skin of a patient; and
(b) a one-way valve assembly mounted to the panel across the opening in the panel, the valve assembly comprising:
(i) a valve base having a central opening through the base and a plurality of valve openings through the base spaced circumferentially about the central opening;
(ii) an annular valve member mounted to the base member about the central opening so as to overlie the valve openings, at least when the valve is closed, the valve member being configured so as to permit air and/or other fluids to flow outwardly through the valve openings whilst preventing air and/or other fluids from flowing inwardly through the valve openings;

(iii) a valve housing mounted to the valve base so as to encase the valve member, the valve housing having a central opening in alignment with the central opening in the base and a plurality of valve outlet openings circumferentially spaced about the central opening;

(iv) means extending between the central opening in the base and the central opening in the cover to define a continuous, fluid tight passage through the valve assembly; and (v) a removable closure member for selectively closing the central passage.

30. A medical dressing, the dressing comprising:

(a) a flexible panel having an inner surface and an outer surface and defining an opening therethrough, the panel having adhesive on the inner surface for attaching the panel to the skin of a patient; and (a) a one-way valve assembly mounted to the panel to control the flow of air and/or other fluids through the opening; the valve assembly comprising:

(i) a valve base having a central portion and an outer flange portion, the base defining at least one valve opening through the central portion of the base, the central portion of the base extending through the opening of the panel with the flange portion abutting the inner surface of the panel about the opening in the panel;

(ii) a valve member mounted to the valve base to regulate the flow of air and/or other fluids through the at least one valve opening, the valve member being configured so as to permit air and/or other fluids to flow outwardly through the at least one valve opening whilst preventing air and/or other fluids from flowing inwardly through the at least one valve opening;

(iii) a valve cover mounted to the valve base, the cover comprising a housing portion in which the central portion of the valve base is received and an outer flange portion which opposes the flange portion on the base and which abuts the outer surface of the panel about the opening in the panel, the housing portion having at least one valve outlet opening therein through which air and/or other fluids flowing outwardly through the at least one valve opening in the base can pass to exit the valve assembly in use;

(iv) the valve base and the valve housing defining a further passage through the valve assembly which further passage opens through the central portion of the valve base, the further passage being fluidly isolated from the remainder of the valve assembly and unobstructed by the valve means; and (v) the valve assembly comprising a removable closure member for selectively closing the further passage.

* * * * *